(12) United States Patent
Fish et al.

(10) Patent No.: US 6,827,080 B2
(45) Date of Patent: Dec. 7, 2004

(54) PRESSURE ACTIVATED REACTION VESSEL AND PACKAGE

(75) Inventors: Jeffrey E. Fish, Dacula, GA (US); Naveen Agarwal, Atlanta, GA (US); Rosann Marie Kaylor, Cumming, GA (US); Lei Huang, Duluth, GA (US); John Shuty, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 106 days.

(21) Appl. No.: 10/263,503

(22) Filed: Oct. 3, 2002

(65) Prior Publication Data

US 2004/0065315 A1 Apr. 8, 2004

(51) Int. Cl.[7] ............................................. A62M 35/00
(52) U.S. Cl. ........................ 126/263.01; 126/263.09; 206/223
(58) Field of Search .......... 126/263.01, 263.05–263.09; 206/219, 222, 210, 223; 424/44, 402; 604/291, 303, 304; 62/4, 457.1, 457.9; 165/46

(56) References Cited

U.S. PATENT DOCUMENTS

| | | | |
|---|---|---|---|
| 3,585,982 A | | 6/1971 | Hollinshead |
| 3,683,889 A | | 8/1972 | Hoffman |
| 3,804,077 A | | 4/1974 | Williams |
| 4,067,313 A | | 1/1978 | Donnelly |
| 4,088,751 A | | 5/1978 | Kenkare et al. |
| 4,694,973 A | | 9/1987 | Rose et al. |
| 4,700,048 A | | 10/1987 | Levy |
| 4,784,678 A | * | 11/1988 | Rudick et al. ............... 206/219 |
| 4,943,705 A | | 7/1990 | Halloran |
| 5,210,396 A | | 5/1993 | Sanders |
| 5,231,266 A | | 7/1993 | Warren |
| 5,542,418 A | | 8/1996 | James |
| 5,553,741 A | | 9/1996 | Sancoff et al. |
| 5,699,902 A | * | 12/1997 | Sperry et al. ............... 206/219 |
| 5,738,082 A | | 4/1998 | Page et al. |
| 6,179,162 B1 | | 1/2001 | Motsenbocker |
| 6,289,889 B1 | | 9/2001 | Bell et al. |
| 6,392,200 B1 | | 5/2002 | Nakamura et al. |
| 6,547,063 B1 | * | 4/2003 | Zaveri et al. ............... 206/219 |
| 2002/0017310 A1 | | 2/2002 | Gruenbacher et al. |
| 2002/0020407 A1 | | 2/2002 | Wohland et al. |
| 2002/0032135 A1 | | 3/2002 | Verdrel-Lahaxe et al. |
| 2002/0174863 A1 | * | 11/2002 | Saric et al. ............. 126/263.05 |
| 2003/0000517 A1 | * | 1/2003 | Jospeh et al. .................. 165/46 |

FOREIGN PATENT DOCUMENTS

| | | |
|---|---|---|
| DE | 35 01 733 A1 | 7/1986 |
| EP | 1 164 092 A2 | 12/2001 |
| JP | 09094167 | 4/1997 |
| WO | WO 00/43286 | 7/2000 |
| WO | 01/26528 | 4/2001 |
| WO | 02/30251 | 4/2002 |

* cited by examiner

Primary Examiner—Sara Clarke
(74) Attorney, Agent, or Firm—Pauley Petersen & Erickson

(57) ABSTRACT

This invention relates to a reaction vessel constructed of a flexible material including at least two reactant chambers containing two isolated reactants. The reactant chambers and reactants are separated by a frangible seal which opens under pressure, allowing the reactants to mix and react. The reaction produces a desired reactive effect on the environment surrounding the reaction vessel and any articles in that environment. A package in combination with a reaction vessel can be used to cause a reactive effect on an article within the package. The reactive effect can include a temperature change of the article or foaming a material to coat the article.

31 Claims, 3 Drawing Sheets

PRESSURE ACTIVATED REACTION VESSEL AND PACKAGE

FIELD OF INVENTION

The present invention relates to a self-contained reaction vessel containing two reactants separated by a frangible seal. Applying pressure to the reaction vessel ruptures the frangible seal and the reactants mix and react to produce a desired reactive effect, such as heating or cooling. The reaction vessels can be used in combination with packages for containing pre-moistened towels, wipes, and other articles.

BACKGROUND OF THE INVENTION

Hot and cold packs known in the art use two reactants separated by a breakable material that, when broken prior to use, causes the mixing and, thereby, the chemical reacting of the reactants. The resulting reaction can be exothermic or endothermic, and the hot or cold packs can be applied to a localized region on a person's body. U.S. Pat. No. 3,804,077, issued to Williams, and U.S. Pat. No. 4,067,313, issued to Donnelly teach several embodiments of hot or cold packs. The hot or cold packs can be used to treat injuries, warm hands or feet, or be placed next to food items to retain or achieve desired temperatures.

U.S. Pat. No. 6,289,889, issued to Bell et al., teaches using a flexible heating element having two chambers containing two reactants separated by a frangible seal in combination with a product pouch. Rupturing the frangible seal causes an exothermic reaction which heats the product pouch. The product pouch can contain various materials including liquids, solids, or powders. The product pouch can be porous and contain coffee or tea leaves for simultaneously steeping and heating coffee and tea.

Although a number of self-heating and self-cooling hot and cold packs are known and used in various ways, the basic principles of separating two reactants in separate compartments by a breakable material or seal prior to use can be expanded to include new reactants that provide additional reactive effects in addition to heating and cooling. In addition there is a need for improved packaging for more efficiently using the principles of the two chamber chemical reactant vessel, whether for heating, cooling, or otherwise.

SUMMARY OF THE INVENTION

The present invention relates to reaction vessels and the use of the reaction vessels with products and product packaging. The invention provides a reaction vessel including at least two reactant chambers. The reactant chambers are constructed at least in part of a flexible material. A first reactant chamber contains a first reactant and a second reactant chamber contains a second reactant. The first and second reactant chambers are adjacent to each other and separated by a frangible seal. The frangible seal separates the first and second reactant chambers thereby isolating the first and second reactants. Prior to use, pressure is applied to the flexible material of one of the first and second reactant chambers to open or rupture the frangible seal. The opening of the frangible seal allows the mixing of the first and second reactants. The first and second reactants chemically react upon contact. The reaction produces a desired reactive effect on an environment surrounding the reaction vessel and any articles in that environment.

The reaction can be exothermic or endothermic. An exothermic reaction would produce heat that would cause the reactive effect of heating a surrounding environment or article. Oppositely, an endothermic reaction would adsorb energy from the surrounding environment, thereby causing a cooling reactive effect. The reaction vessel can include a conductive material such as a metal foil as a backing material to provide a more efficient energy transfer. "Conductive material" refers to a material that is thermally conductive, or in other words, conducts thermal energy or heat. By using an insulating material on a side of the reaction vessel opposite the conductive material, efficiency can again be improved, and the heating or cooling effect can be maximized in a direction towards an article compartment in combination with the reaction vessel.

The reaction vessels of this invention can include reactants that produce additional reaction byproducts or reactive effects. The reactants can react to produce a gas such as oxygen or carbon dioxide, or react by foaming. The reactant chambers can include additional compositions that are activated or otherwise improved through foaming of the reactants. Examples of such foamable compositions include foaming skin washes and foaming disinfectants. The reaction vessel can include a gas-permeable membrane to allow the produced gas to escape the reaction vessel. The gas can be used for reactive effects such as carbonating a beverage or to foam a material in an article compartment in combination with the reaction vessel. If the reactants produce a foaming reaction, the reaction vessel can include an access means such as a tear notch for removing the foamed material, or a porous material that allows the foamed material to exit the reaction vessel.

This invention also relates to packaging for effectively and efficiently using the reaction vessel and the reactive effects produced by the reaction vessel. In one embodiment of this invention, a package for containing an article, such as a pre-moistened towel, includes an article compartment. The article compartment has a first side and a second side opposite the first side. The first side includes a removable portion for access to the article compartment for removing the article therein. The package includes a reaction vessel in combination with the second side of the article compartment. The reaction vessel can be any reaction vessel of the invention producing any of the reactive effects. The reaction vessel includes a first reactant chamber containing a first reactant and a second reactant chamber containing a second reactant. A frangible seal separates the first and second reactant chambers and isolates the reactants until just prior to use.

At least one of the first and second reactant chambers includes a flexible material. Pressure applied to the flexible material of one of the reactant chambers opens the frangible seal and causes the first and second reactants to mix and react. The reaction causes a reactive effect in the article compartment and thereby on the article contained therein. When the reactive effect is a temperature change produced by an exothermic or endothermic reaction, the second side of the article compartment can include a conductive material. When the reactants produce a gas, the second side can include a gas-permeable membrane. Gas-permeable membranes serve to release an evolved gas of the reaction, or may let atmospheric oxygen into the system as a reactant in an oxidation reaction. The gas can enter the article compartment and foam a material contained in the article compartment. The foamed material in turn is picked up by the article for use. Reactants can be chosen that produce a combination of reactive effects such as heating or cooling and producing a gas or foam.

Reactant combinations useful for producing an exothermic reactions are water and calcium chloride or calcium oxide. Water combined with either ammonium, ammonium nitrate, or urea are reactant combinations that produce endothermic reactions. Acid and base combinations, such as citric acid and sodium carbonate or sodium bicarbonate, and acetic acid and sodium bicarbonate, can be used to produce a gas in the reaction vessel. Other reactant combinations include oxidizers and reducers, color changing reactants, and disinfectant-generating reactions, such as those which produce chlorine dioxide ($ClO_2$), chlorine, or iodine, to provide in situ disinfection.

In another embodiment of this invention, a package for containing an article, such as a pre-moistened wipe or facial mask, includes an article compartment for containing an article. The article compartment has an article compartment body extending between a first end and a second end opposite the first end. The second end of the first compartment includes a removable portion for access to the article compartment for removing the article therein. The package further includes a reaction vessel in combination with, and desirably surrounding, the article compartment body. The reaction vessel including a first reactant chamber containing a first reactant is separated from a second reactant chamber containing a second reactant by at least one frangible seal. The reaction vessel is made from a flexible material. Pressure applied to the flexible material opens the frangible seals and the first and second reactants mix and react. The reaction can produce numerous reactive effects on the article as disclosed herein.

BRIEF DESCRIPTION OF THE DRAWINGS

These and other objects and features of this invention will be better understood from the following detailed description taken in conjunction with the drawings, wherein.

DESCRIPTION OF PREFERRED EMBODIMENTS

This invention relates to a reaction vessel having two or more reactant chambers for isolating two or more reactants. The reactant chambers are separated by a frangible seal that can be broken to allow the reactants to mix and react. Prior to mixing, the reactants are isolated and stable in their respective reactant chambers. The reaction upon mixing can include exothermic, endothermic, and gas-producing reactions, thereby producing a desired reactive effect. "React," "reacting," or "reaction" refers to any chemical reaction, hydration, or solvation of two or more components. "Reactant" refers to a component that will react when in the presence of one or more additional components, and can include any material, chemical, solvent, or solution. "Reactive effect" refers to a physical or chemical change in the environment surrounding the reaction vessel, an article compartment in combination with the reaction vessel, or an article, material, and/or product in the article compartment. Examples of reactive effects include a temperature change, producing a gas, and foaming of a foamable material through gas production. The reactant chambers are desirably constructed at least in part of a flexible material. "Flexible" refers to a material that is easily deformed, flexed, bent, or folded under pressure or force applied by the fingers or hands. The frangible seal can be broken by pressing, squeezing, or twisting one of the flexible reactant chambers. The reaction vessel can be used to heat, cool, or provide various gases, and can have numerous commercial applications.

The reaction vessel is preferably constructed of material appropriate for containing the reactants contained therein. The reaction vessel can be made of flexible material, such as a thermoplastic membrane enclosing the reactant chambers. Desirably, the flexible material will be suitable for holding the reactants contained therein and will not be corroded or otherwise degraded by the reactants. The reactants can be solids, liquids, gases, and combinations thereof. One such combination includes one liquid reactant and one solid reactant. The more impermeable the flexible material is to the contained reactant, the longer the shelf life of the reaction vessel. Examples of flexible materials useful in this invention include plastic-injection molded, molded, cast, and blown polymer films. The flexible membrane should have a thickness of about 0.001 to 0.32 centimeters, desirably about 0.007 to 0.025 centimeters.

Figure 1:
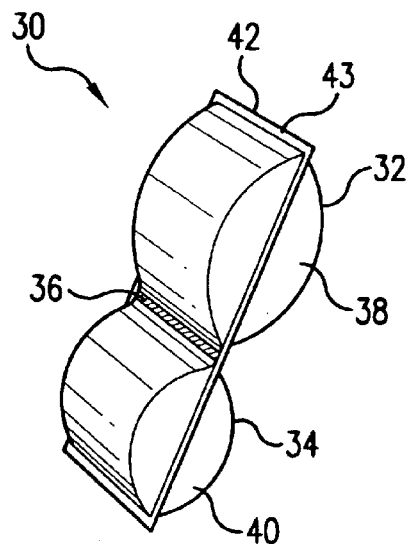
FIG. 1 shows a perspective view of a reaction vessel according to one embodiment of this invention.

FIG. 1 shows one embodiment of a reaction vessel 30 according to this invention. The reaction vessel 30 includes first reactant chamber 32 adjacent to second reactant chamber 34. First reaction chamber 32 encloses and contains a first reactant 38. Second reactant chamber 34 contains a second reactant 40. The first reactant 38 and the second reactant 40 are desirably stable when isolated in the respective reactant chamber and will react with each other when mixed to produce a desired reactive effect. Examples of reactive effects include heating, cooling, and producing various gases such as oxygen or carbon dioxide.

The first reactant chamber 32 is separated from second reactant chamber 34 by a frangible seal 36. The frangible seal prevents the first reactant 38 from contacting the second reactant until the frangible seal 36 is opened. The frangible seal 36 can be constructed from plastic, films, metal foils, and other suitable materials, as well as thermal bonds and adhesive bonds that unbond under pressure. The film or foil frangible seals should have a thickness of about 0.001 to 0.05 centimeters, desirably about 0.002 to 0.02 centimeters. The frangible seal 36 may be scored or otherwise weakened to cause rupture or tear initiation in a predetermined location of the seal.

FIG. 1 shows the entire reaction vessel 30 constructed of a flexible material. Pressure applied to the flexible material by squeezing, pressing, or twisting ruptures the frangible seal 36 and allows the first and second reactants to come into contact. Desirably, both the first reactant chamber 32 and the second reactant chamber 34 are constructed at least in part of the flexible material.

The reaction vessel of FIG. 1 is constructed by bonding two flexible films around a peripheral edge 42, by forming a seal to contain the reactants within the reaction vessel 30. The peripheral edge 42 of the reaction vessel can be bonded by various bonding methods known in the art, such as thermal bonding, lamination bonding, ultrasonic bonding, or adhesive bonding. Thermal bonding is achieved through a combination of heat and pressure applied to the bond area. Ultrasonic bonding uses pressure and high frequency sonic energy directed through a horn that contacts the area to fuse thermoplastic materials. A second, weaker bond by one of these methods can also be used to form the frangible seal 36, thereby separating the first reactant chamber 32 from the second reactant chamber 34. Applying pressure to the flexible material will rupture the weaker bond of the frangible seal 36 and will not rupture the bond around the peripheral edge 42 of the reaction vessel 30. The opening of the frangible seal 36 results in the first and second reactant chambers 32, 34 combining as one larger chamber. Thermal bonding can be used for both the frangible seal 36 and the non-frangible seal 43 of the peripheral edge 42 by varying the temperature, pressure, and time of the sealing apparatus. The bond of the frangible seal 36 has a suitable width of about 0.15 to 2.0 centimeters, more suitably about 0.30 to 1.30 centimeters.

Figure 2:
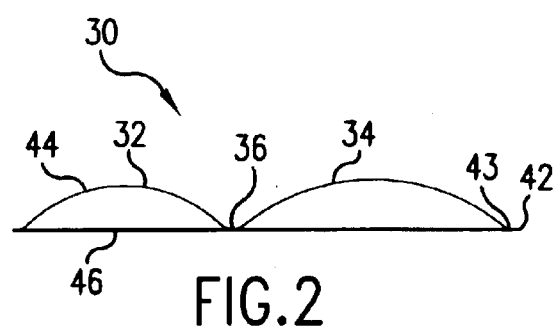
FIG. 2 shows a side view of a reaction vessel according to one embodiment of this invention.

The reaction vessel 30 can be constructed of various materials and in various configurations. For instance, the reaction vessel 30 can be made entirely of a flexible material or, as shown in FIG. 2, the flexible material 44 can be bonded to a backing 46. "Flexible material" refers to a material such as film or membrane that is easily flexed, bent or folded. The flexible material will flex under pressure such as from pressing or twisting the flexible material. The flexible material 44 is bonded to the backing 46 around peripheral edge 42 and at frangible seal 36. The frangible seal 36 separates the first reactant chamber 32 and the second reactant chamber 34. The frangible seal 36 is a weaker bond than the bond around the peripheral edge 42. Therefore, pressure applied to the flexible material 44 will open frangible seal 36, allowing the reactants to mix, and not rupture the bond around the peripheral edge 42.

The backing 46 provides support for flexible material 44 during production and packaging of reaction vessel 30. The backing 46 is desirably a more rigid material than the flexible material 44, such as, for example, a thin sheet of plastic. The backing 46 can also be a thermally-conductive material, such as a metal foil. A conductive backing 46 is particularly useful when the mixed reactants produce an exothermic or an endothermic reaction. The conductive material allows a more efficient energy transfer across the backing 46, thereby maximizing the heating or cooling reactive effect produced by the reaction vessel 30.

In one embodiment of this invention the backing 46 can be a removable access or include a removable access portion section. The first and second reactants 38, 40 can react and form a foaming or disinfecting surface cleaner, an epoxy material, a medicinal composition, or other useful product that needs to be removed from the reaction vessel 30. By opening the access to the reaction vessel 30, the mixed reactants can be scooped out or squeezed out by applying additional pressure on the reactant chambers. An example of an access is a tear-off portion or corner, such as common in condiment packages.

The backing 46 can connect the reaction vessel 30 to the backing of a second reaction vessel at peripheral edge 42. In one embodiment of this invention, two or more reaction vessels 30 are connected at peripheral edge 42 during manufacture by laying a sheet of flexible material large enough to form the two or more reaction vessels 30 to a similar size sheet of backing material. By methods known in the art, the sheet of flexible film material is bonded to the sheet of backing material to form the two or more reaction vessels 30. The two or more reaction vessels 30 can be cut apart for individual packaging or outlined by a perforated cut along the peripheral edge 42 of each reaction vessel 30. By perforating the peripheral edge 42 between the reaction vessels, the reaction vessels can be connected while in the shipping or storage container and detached from each other by the user for individual use. By this method various numbers of reaction vessels can be connected with a perforated peripheral edge 42 for sale in containers of various sizes containing various quantities.

Figure 3:
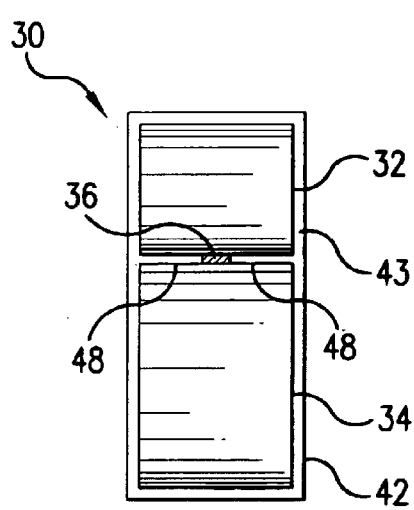
FIG. 3 shows a top view of a reaction vessel according to one embodiment of this invention.

The first and second reactants 38, 40 are preferably in stoichiometric quantities so that after use the reaction vessel 30 contains no unreacted reactants. The reaction rate of the first and second reactants 38, 40 can be controlled by the amount and the reaction characteristics of the reactants as well as the size of the frangible seal 36. FIG. 1 shows the frangible seal 36 extending across the width of the first and second reactant chambers 32, 34. FIG. 3 shows the frangible seal 36 as extending across a portion of the width of the first and second reactant chambers 32, 34. Non-frangible seals 48 extend the additional width of the first and second reactant chambers 32, 34 beyond the frangible seal 36. The non-frangible seals 48 can be the same form of bonding as around the peripheral edge 42.

Figure 4:
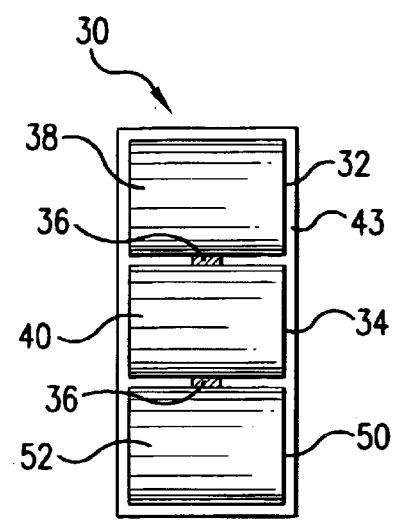
FIG. 4 shows a top view of a reaction vessel according to one embodiment of this invention.

The reaction vessels of this invention can include more than two reactant chambers for containing more than two reactants that are isolated until mixed. As shown in FIG. 4, the reaction vessel 30 includes the first reactant chamber 32 containing the first reactant 38, the second reactant chamber 34 containing the second reactant 40, and a third reactant chamber 50 containing a third reactant 52. Two frangible seals 36 separate the three reactant chambers. Pressure placed on the first reactant chamber 32 will open the frangible seal 36 between the first reactant chamber 32 and the second reactant chamber 34, and mix the first reactant 38 and the second reactant 40. Similarly, pressure placed on the third reactant chamber 50 will open the frangible seal 36 between the third reactant chamber 50 and the second reactant chamber 34, and mix the third reactant 52 and the second reactant 40. Applying pressure to the second reactant chamber 34 will open both frangible seals 36. Through applying pressure to selective reactant chambers, the first reactant 38, the second reactant 40, and the third reactant 52 can be mixed sequentially or simultaneously. Pressure can be applied by pressing, squeezing, or twisting the reactant chambers. The amount of pressure needed to open the frangible seal is dependent on the strength of the frangible seal 36.

In one embodiment of the reaction vessel 30 of this invention, the first reactant 38 and the second reactant 40 react when mixed to produce a gas. At least one of the first reactant chamber 32 and the second reactant chamber 34 includes a gas-permeable membrane. "Gas-permeable" refers to a membrane having a structure through which 20 to 30,000 cubic centimeters per minute per meter squared gas may pass. The gas produced by the reaction of the first reactant 38 and the second reactant 40 permeates the gas-permeable membrane. Examples of gas-permeable membranes useful in this invention include microporous films, perforated film or foil, sintered metal, nonwovens, and semi-permeable or permeable membranes. When the reaction vessel 30 includes a gas-permeable membrane the first reactant 38 and the second reactant 40 can be solids, liquids, or combinations thereof. When liquid reactants are used, the gas-permeable membrane is desirably a liquid impermeable, gas permeable membrane. "Liquid-impermeable" refers to a membrane having a hydrostatic head of greater than 10 centimeters.

In one embodiment of this invention, the first reactant 38 is a solid and the second reactant 40 is water or an aqueous solution. If the second reactant 40 is water or a solution, then the second reactant can evaporate through a liquid-impermeable, gas-permeable membrane over time. A liquid-impermeable, gas-permeable membrane in combination with a reactant chamber containing a liquid reactant may lower the shelf life of the reaction vessel 30. Therefore, it is desirable that only the first reactant chamber 32 includes a liquid-impermeable, gas-permeable membrane. The solid first reactant 38 can be enclosed within the liquid-impermeable, gas-permeable membrane of the first reactant chamber 32. The second reactant chamber 34 includes a liquid-impermeable, gas-impermeable membrane and contains the aqueous second reactant 40. Upon opening of the frangible seal 36 the second reactant 40 contacts the first reactant 38 and produces a gas. The produced gas escapes through the gas-permeable membrane of the first reactant chamber 32. Although evaporation from the second reactant 40 can occur after the opening of the frangible seal 36, the effect of the slow evaporation is likely to be negligible.

Using a variation of the reaction vessel 30 shown in FIG. 4, two liquid reactants can be used. The first reactant chamber 32 and the third reactant chamber 48 contain liquid reactants 38, 50. The second reactant chamber 34 includes a liquid-impermeable, gas-permeable membrane and contains no reactant. The second reactant chamber 34 will likely, however, contain an amount of air that has passed through the gas permeable membrane from the external environment. Upon opening of the two frangible seals 36, the first reactant 38 and the third reactant 50 mix in the second reactant chamber to produce a gas that permeates the liquid-impermeable, gas-permeable membrane of the second reactant chamber 34. This embodiment is also useful for gas reactants, substituted for one or both of the liquid reactants, or for reactants that react in the presence of air.

Examples of reactant combinations useful in this invention for producing a gas upon reaction include acid and base combinations, such as citric acid and sodium carbonate or sodium bicarbonate, and acetic acid and sodium bicarbonate. Of these combinations the reactants sodium carbonate and sodium bicarbonate can be solid and mixed with solutions of citric acid or acetic acid.

In another embodiment of this invention, the reactants mix and react by foaming. The reactants can include additional foamable compositions in the reactant chambers such as lotions or cleaning agents that are foamed by the reactants. The foamable compositions can then be removed from the reaction vessel by the reaction vessel user. Examples of foamable materials include foamable facial cleaners, lotions, and soaps, as well as foamable surface cleaners, anti-microbial, or disinfectants. In one embodiment the reaction vessel includes a third reactant chamber in combination with the first and second reactant chambers, such as in FIG. 4. The third reactant chamber 50 is separated from at least one of the first and second reactant chambers 32, 34 by an additional frangible seal 36. The third reactant chamber 50 can be empty and includes a porous material which the foamable composition can permeate. As the reaction of the first and second reactants 38, 40 produces the foamable composition, the frangible seal 36 separating the third reactant vessel 50 is opened and the foamable composition enters the third reactant chamber 50 and permeates the porous material. The reaction vessel 30 can include various sizes and configurations of the first, second, and third reactant chambers. For example, the second reactant chamber can be empty and include the porous material and the reactants from first and third reactant chambers 32, 50 can enter the second reactant chamber 34 and react. The porous material can be a woven or nonwoven material or a sponge material for applying the foamable composition to the user's face or other surface such as a countertop. The reaction vessel 30 can also be combined with a sponge that extends the length of the reaction vessel 30 for application of the foamable composition.

The reaction vessels of this invention can include various reactants that provide numerous reactive effects. The reaction vessels of this invention can be used in combination with various commercial products. The reaction vessels containing reactants that produce exothermic or endothermic reactions can be used to heat or cool products including food products, beverages, lotions, cosmetics, and articles such as woven or nonwoven towels, wipes, therapeutic patches or wraps, gloves, and fabric facial masks. The gas-producing reactants can be used, for example, to inflate inflatable products such as life rafts, produce carbon dioxide for carbonated beverages or a fire extinguisher, and produce oxygen for a tankless breathing apparatus. The reactants can also react to produce foaming or disinfecting surface cleaners, medical treatments, epoxies, lotions, creams, or other cosmetic products.

Figure 5:
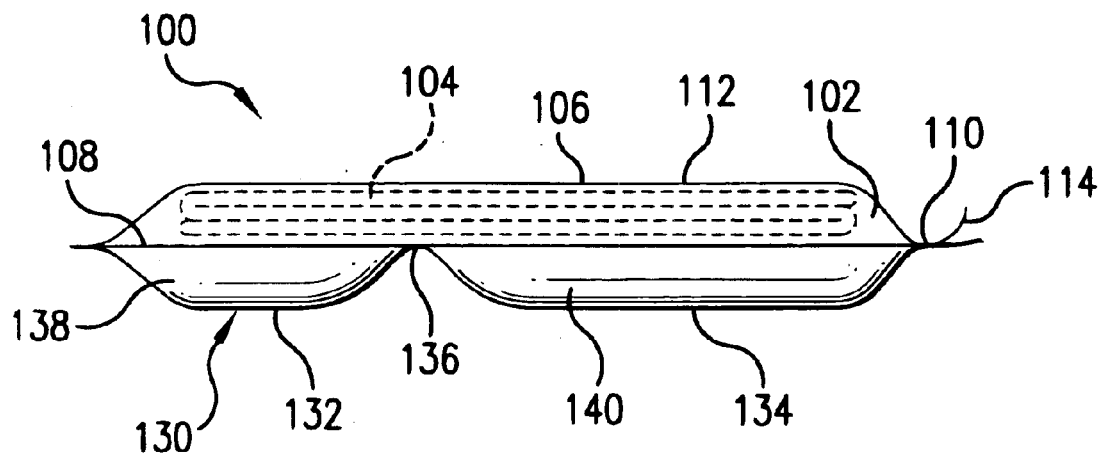
FIG. 5 shows a side view of a package according to one embodiment of this invention.

In one embodiment of this invention the reaction vessels of this invention are used in combination with a package for containing an article such as a pre-moistened wipe, towel, glove, or facial mask. The package includes a reaction vessel containing two or more reactants that when mixed, react and cause a desired change in the article. In one embodiment of this invention, as shown in FIG. 5, package 100 includes an article compartment 102 containing article 104. The article compartment 102 has first side 106 opposite second side 108. The first side 106 and second side 108 are joined by a seal 110. The seal 110 desirably joins an entire peripheral edge of first side 106 to an entire peripheral edge of the second side 108. In one embodiment of this invention, first side 106 and second side 108 are gas-impermeable and, when joined by the seal 110, desirably form an air-tight article compartment 102. An air-tight, vapor-impermeable article compartment 102 is desired when the article 104 is pre-moistened so the article 104 does not dry out. The more air-tight the article compartment 102 and the reaction vessel 130, the longer the shelf life of the package 100. The first side 106 and the second side 108 can be joined by various means known in the art, such as adhesive bonding, thermal bonding, and ultrasonic bonding.

The first side 106 includes a removable portion 112. The removable portion 112 allows access to the article compartment 102 to remove the article 104. In one embodiment of this invention the removable portion 112 is the entire first side 106, which separates from the second side at the seal 110. Removal of the removable portion 112 can be made simple by a flap 114. In FIG. 5, flap 114 is shown as an extension of the removable portion 112 extending beyond the seal 110 at one edge of the package 100. By pulling the flap 114 towards the opposite edge, the seal 110 is broken and the first side 106 is removed. In one embodiment of this invention, the removable portion 112 is removed to expose the article 104 which is not removable. The article 104 may be a heated wiper which, during use, continues to receive the reactive effect from the reacting components in chamber 140 as the article stays in contact with the second side 108.

The package 100 of this invention includes a reaction vessel 130 in combination with the article compartment 102. The reaction vessel 130 is shown in FIG. 5 as adjacent to the second side 108 of the package 100. The reaction vessel 130 includes first reactant chamber 132 containing first reactant 138 separated from second reactant chamber 134 containing second reactant 140 by frangible seal 136. At least one of the first and second reactant chambers 132, 134 include a flexible material. When pressure is applied to the flexible material of the first reactant chamber 132 or second reactant chamber 134, the frangible seal 136 is opened and the first reactant 138 and the second reactant 140 mix and react. The reaction of the first reactant 138 and the second reactant 140 produce a reactive effect on the article 104 inside the article compartment 102 of the package 100. The reactive effect on the article 104 is dependent on the reactants contained in the reaction vessel 130.

The package 100 of FIG. 5 shows the article compartment 102 and the reaction vessel 130 as sharing a common side. The article compartment 102 and the reaction vessel 130 are both bonded to second side 108. In other words, the first side of the article compartment 102 is attached to one face of second side 108 and the opposite face of the second side 108 is the backing to the reaction vessel 130. This embodiment has the advantage of fewer materials and production steps, and more efficient temperature change of the article 104 in the article compartment 102 as a result of the reaction in the reaction vessel 130.

The reaction of the reactants in the reaction vessel 130 causes a reactive effect on the article in the article compartment. One such reactive effect is a temperature change of the article 104 in the article compartment 102. Reactants that produce an exothermic reaction produce the reactive effect of heating the article 130. Examples of reactant combinations that produce heat include water and one of calcium chloride, calcium oxide. Using water as one of the reactants is desired as the thermal conductivity of water helps heat the walls of the vessel faster than dry reactants with interstitial air spaces. Other reactants known in the art for use in reaction which produce heat include, without limitation, quick lime, sodium hydroxide, cobalt, chromium, iron, iron hydroxide, magnesium, molybdenum, tin oxide (II), titanium, sodium, potassium, magnesium chloride, and anhydrous calcium chloride. Reactants that produce an endothermic reaction produce the reactive effect of cooling the article 130. Examples of reactant combinations that produce endothermic reactions that can cool the article include water and one of ammonium, ammonium nitrate, urea, ammonium sulfurate, potassium nitrate, or sodium thiosulfate. The second side 108 can be a conductive material that readily transfers thermal energy. The conductive second side 108 provides more efficient heating and cooling of the article 104. Examples of useful conductive materials include metal foils, such as aluminum foil, and thin films.

In another embodiment of this invention the reaction vessel 130 includes reactants that produce a gas. The second side 108 can include a gas permeable membrane to allow the gas produced by the reaction in the reaction vessel 130 to enter the article chamber 102. The gas can provide the reactive effect of foaming a foamable material in the article compartment 102. The foamed material can be a foaming skin treatment or cleaning material or a foaming surface cleaning material that is applied by the article 104. Examples of foamable materials include surfactants with gas forming agents such as sodium dodecyl sulfate with citric acid combined with sodium carbonate, sodium dodecyl sulfate with citric acid combined with sodium bicarbonate, polyurethane, as well as polystyrene, polyethylene, polyvinyl chloride, polyamide, and silicone.

Desirably, the gas permeable membrane is also liquid-impermeable. As discussed above, where the first reactant 138 is water or in solution and the second side 108 is a liquid-impermeable, gas-permeable membrane, the first reactant 138 can evaporate through second side 108. The evaporation of the liquid first reactant 138 is limited in the reaction vessel 130 shown in FIG. 5 when the first side of the package 100 is gas-impermeable, thereby rendering a closed system. However, the gas of first reactant 138 can enter the second reactant chamber 134 and may condense under certain conditions to react with at least a portion of the second reactant 140 before the activation of the reaction vessel 130 by the user. To avoid the evaporation of the liquid first reactant 138, the second side 108 can include a liquid-impermeable, gas-impermeable film in combination with the first reactant chamber 132 and a liquid impermeable, gas permeable membrane in combination with the second reactant chamber 140. Alternatively, the second side 108 can be a gas-permeable membrane and an additional gas-impermeable film can be included between the first reactant chamber 132 and the second side 108.

Figure 6:
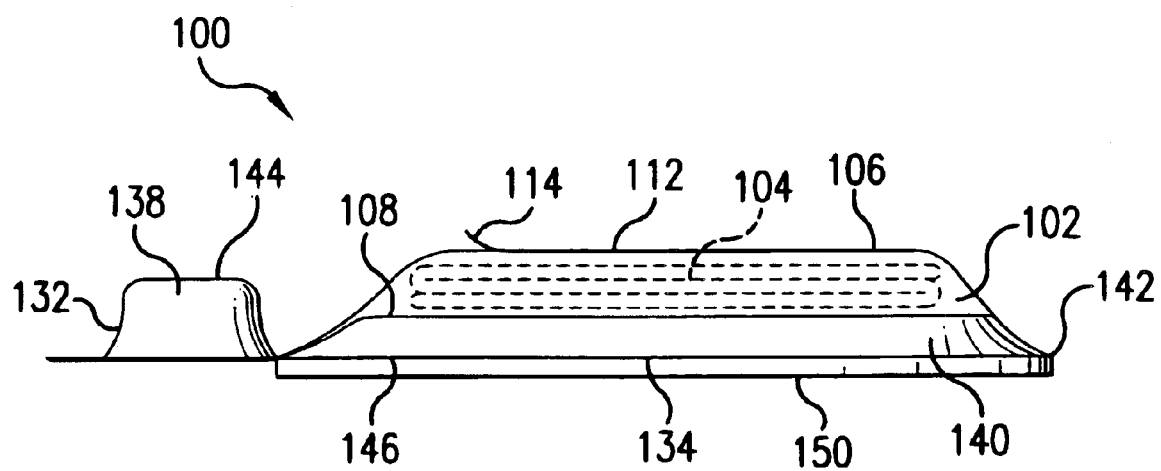
FIG. 6 shows a side view of a package according to one embodiment of this invention.

The package 100 shown in FIG. 6 shows the article compartment 102 aligning with the second reactant chamber 134. The article chamber 102 does not extend over the first reactant chamber 132. The second side 108 can be a liquid-impermeable, gas-permeable membrane between the first side 106 and the second reactant chamber 134. The second reactant chamber 134 desirably contains a solid second reactant 140, although the second reactant chamber can contain a liquid second reactant 140 as evaporation would be limited due to the closed system of package 100. A backing 146 is joined to the second side 108 at edge 142 to enclose the second reactant chamber 134. The backing 146 extends beyond the second reactant chamber 146 on one side to also provide a backing for the first reactant chamber 132. The backing 146 is desirably made of a semi-rigid material such as plastic to provide support for both the first reactant chamber 132 and the second reactant chamber 134. The first reactant chamber 132 includes a flexible liquid-impermeable, gas-impermeable material 144. The article compartment 102 is formed by bonding the first side 106 to the second side 108. FIG. 6 also shows the removable portion 112 as less than the entire first side 106. The removable portion 112 can be a film that covers an access hole in first cover. The removable portion 112 is adhesively bonded to the first side 106 and can be peeled off the first side 106 by flap 114. The package of FIG. 6 can alternatively include the removable portion 112 as shown of FIG. 5.

In one embodiment of this invention, the article 104 is a small towel. The towel can be made from nonwoven thermoplastic fibers or woven or knitted natural fibers, or dry-laid or wet-laid fibers as in paper. The towel can be pre-moistened for use in cleaning a user's hands, face, or other body parts, and can include additional therapeutic agents such as Vitamin E, cleaning agents such as facial soaps, and moisturizing agents. The towel can also be for cleaning surfaces such as kitchen and bathroom counters and can include additional cleaning agents such as soaps, disinfecting agents, and deodorizing agents. The towel may be heated by the reaction, and then removed for use, or it may be used while still in contact with second side 108 so it continues to heat during use. Wipes, facial masks, wraps, and therapeutic patches are other examples of articles 104 that can be contained in the article compartment 102.

The package of FIG. 6 includes an optional insulating layer 150. The insulating layer 150 can also be applied to other embodiments of this invention. The insulating layer 150 is useful when the reaction vessel 130 produces an exothermic or endothermic reaction for heating or cooling the article 104. The insulating layer 150 reduces or eliminates the escape of energy from the reaction vessel 130, thereby providing more efficient heating or cooling of article 104 and an increase in the duration of the effective heating period. Insulating layer 150 includes insulating material such as textile fabric, foam, film, nonwoven, and laminates thereof, as well as synthetic or natural fiber matrices. In another embodiment of this invention, a second article compartment 104 can be substituted for the insulating layer 150 on the opposite side of the reaction vessel 130 from the first article compartment 102. The reaction vessel 130 can contain enough reactants to cause the desired level of reactive effect in two article compartments.

Figure 7:
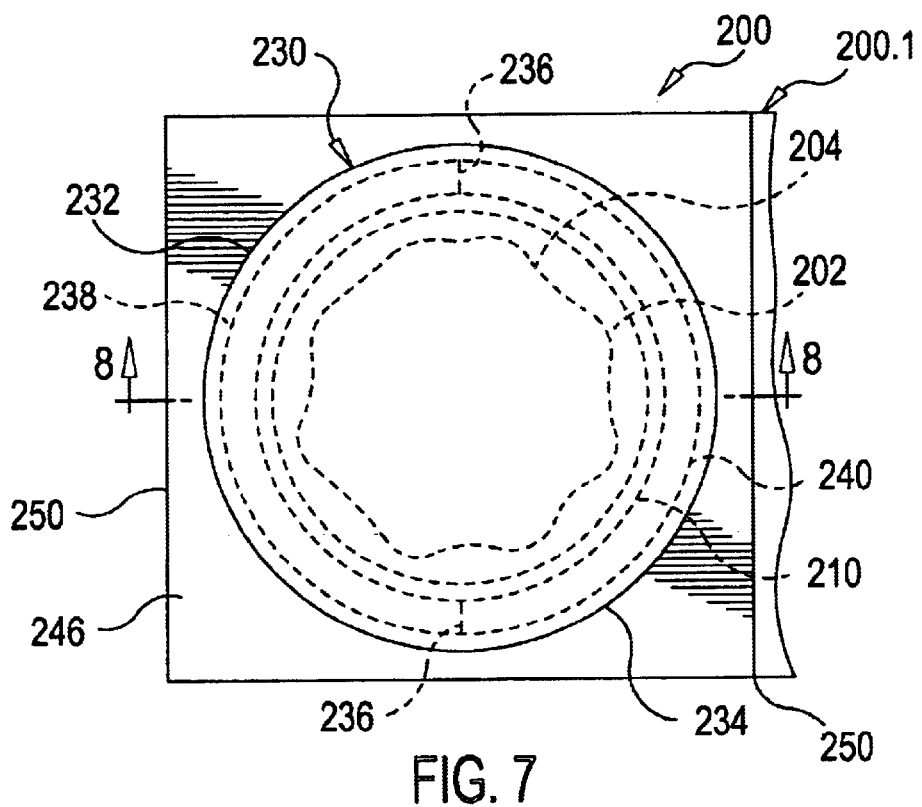
FIG. 7 shows a top view of a package according to one embodiment of this invention.
Figure 8:
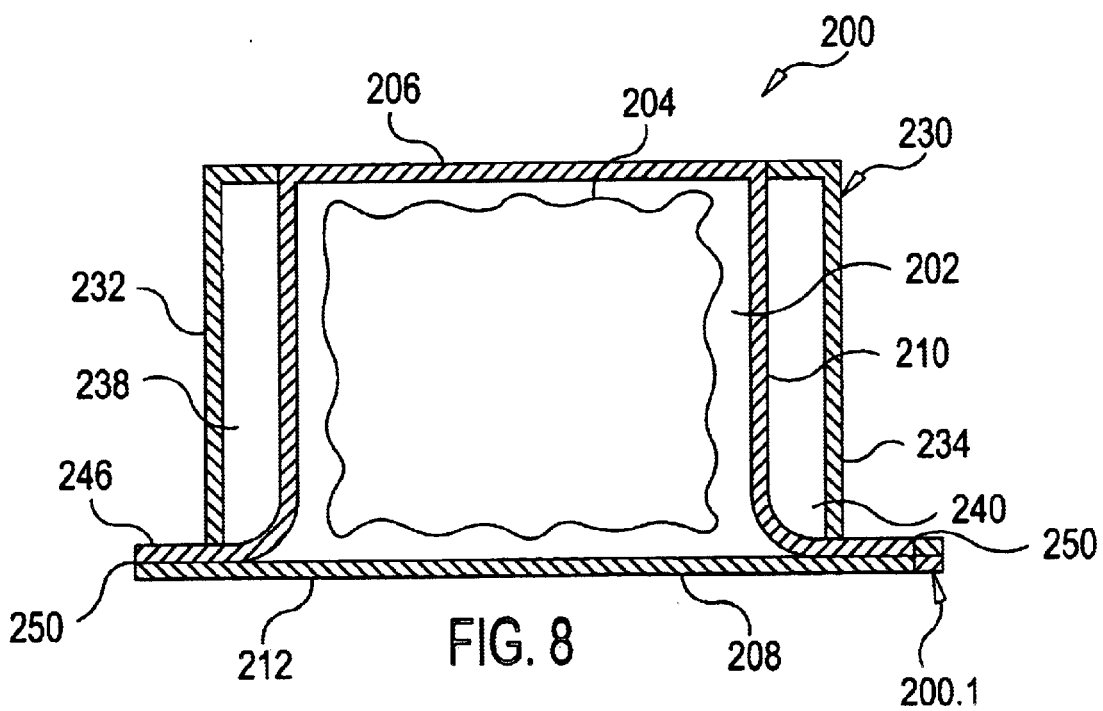
FIG. 8 shows a cross-sectional view of the package of FIG. 7 taken along line 8—8.

FIGS. 7 and 8 show an alternate embodiment of the package of this invention. The package 200 includes an article compartment 202 for containing an article 204. Articles such as wipes, gloves, towels, and facial masks can be folded or otherwise compacted to fit in the article compartment 102. The article compartment 202 has an article compartment body 210 extending between a first end 206 and a second end 208 opposite the first end 206. The article compartment can be cylindrical as shown in FIG. 7 or another shape such as a cube or oval. The second end of 208 of the article compartment 202 includes a removable portion 212 for access to the article compartment 202. The article 204 can be removed from the article compartment 202 by peeling off the removable portion 212. The article 204 can be any article described above, such as a towel or a facial mask. The article 204 can be pre-moistened and can include additional therapeutic agents.

The reaction vessel 230 in FIGS. 7 and 8 includes a first reactant chamber 232 containing a first reactant 238 separated from a second reactant chamber 234 containing a second reactant 240. The reaction vessel 230 surrounds the article compartment body 210 between the first end 206 and the second end 208. As seen in FIG. 8 the reaction vessel 230 does not cover the first end 206 or the second end 208. The first reactant chamber 232 is separated from the second reactant chamber 234 by at least one frangible seal 236. FIG. 7 shows the reaction vessel 230 as having two frangible seals on opposite sides of the article compartment body 210. The frangible seals can include a membrane that extends between the flexible material of the reaction vessel 230 and the article compartment body 210. Alternatively, the frangible seal can include a weak bonding of the flexible material of the reaction vessel 230 to the article compartment body 210. The reaction vessel 230 is made of a flexible material that when squeezed, causes the opening of the frangible seals 236. The reaction vessel 230 could operate with one frangible seal and have the other seal be non-frangible, however, having two frangible seals 236 can provide more efficient mixing of the reactants when the frangible seals 216 are opened. More efficient heating or cooling and a more compact package can be provided by the embodiment shown in FIGS. 7 and 8.

The article compartment body 210 can include a conductive material between the article compartment and the reaction vessel. The conductive material, such as a metal foil, provides for a more efficient thermal energy transfer to or from the article compartment. In another embodiment, the article compartment body 210 can include a gas-permeable membrane to allow gas from the reaction in the reaction vessel 230 to enter the article compartment 202. The gas can cause a material inside the article compartment 202 to foam.

As shown in FIGS. 7 and 8 the second end 208 of the package 200 includes a base 246. The base 246 is desirably a semi-rigid material, such as plastic, for supporting the flexible films and/or membranes used in package 200. The article compartment 202 can be molded out of a thin plastic material having the base 246 extending from the second end 208. As an alternative, the article compartment can be formed from a conductive material such as a metal foil. An opening on the second end 208 can then be covered by removable portion 212 to enclose the article compartment 202. Alternatively, the base 246 can extend from the first end 206 opposite the second end 208 having the removable portion 212. The base 246 extends beyond the reaction vessel 230 and can be an attaching element for attaching to the base of a second similar package 200. The base 246 can attach to an additional similar package 200.1 along each of the edges 250. A plurality of bases 246 can be attached along a perforated edge 250 and easily detached from one another by tearing the perforation.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. A package for containing an article, comprising:

an article compartment having a first side and a second side opposite the first side, the first side including an access portion for access to the article compartment, wherein the article compartment contains the article and the second side includes a gas-permeable material; and a reaction vessel in combination with the second side of the article compartment, the reaction vessel including a first reactant chamber containing a first reactant and a second reactant chamber containing a second reactant, the first and second reactant chambers separated by a frangible seal;

at least one of the first and second reactant chambers including a flexible material;

wherein upon opening of the frangible seal the first and second reactants mix and react, the reaction causing a reactive effect on the article.

2. The package according to claim 1, wherein the second side additionally includes a thermally conductive material.

3. The package according to claim 2, wherein the reactive effect includes a temperature change of the article.

4. The package according to claim 3, wherein the first reactant includes water and the second reactant is selected from a group consisting of calcium chloride, calcium oxide, ammonium nitrate, urea, ammonium sulfurate, potassium nitrate, and sodium thiosulfate.

5. The package according to claim 1, wherein the reaction produces a gas and the reactive effect includes foaming a foamable material in the article compartment.

6. The package according to claim 5, wherein the first reactant is selected from a group consisting of acetic acid and citric acid and the second reactant is selected from a group consisting of sodium carbonate, sodium bicarbonate, and combinations thereof.

7. The package according to claim 1, wherein the article is selected from the group consisting of towels, wipes, masks, wraps, and patches.

8. The package according to claim 7, wherein the article is treated with a therapeutic agent.

9. The package according to claim 7, wherein the article is pre-moistened.

10. A package for containing an article, comprising:
an article compartment including an article compartment body extending between a first end and a second end opposite the first end, the second end of the article compartment including an access for accessing the article compartment, the article compartment containing the article;
a reaction vessel in combination with the article compartment body, the reaction vessel including a first reactant chamber containing a first reactant and a second reactant chamber containing a second reactant, the first and second chambers separated by at least one frangible seal; and
an attaching element for attaching to a second package;
wherein upon opening of the at least one frangible seal the first and second reactants mix and react, the reaction causing a reactive effect on the article.

11. The package of claim 10, wherein the article compartment body includes a conductive material between the article compartment and the reaction vessel, and the reactive effect includes a temperature change of the article.

12. The package of claim 10, wherein the reaction of the first and second reactants produces a gas.

13. The package of claim 12, wherein the article compartment body includes a gas-permeable material between the article compartment and the reaction vessel, wherein the reactive effect includes foaming a foamable material in the article compartment.

14. The package of claim 10, wherein the reaction vessel surrounds the article compartment body between the first and second ends.

15. The package of claim 10, wherein the article is selected from the group consisting of towels, wipes, masks, wraps, and patches.

16. The package of claim 15, wherein the article includes a therapeutic agent.

17. The package of claim 15, wherein the article is pre-moistened.

18. The package of claim 10, additionally comprising a removable portion over the access, wherein the removable portion is peelable.

19. The package of claim 10, wherein the attaching element extends from one of the first end and second end of the article compartment.

20. The package of claim 19, wherein the attaching element comprises perforations.

21. The package of claim 10, wherein the attaching element comprises a base of the article compartment and the base attaches to a base of the second package along a perforated edge.

22. A reaction vessel, comprising:
a first reactant chamber containing a first reactant;
a second reactant chamber containing a second reactant;
a third reactant chamber in combination with the first and second reactant chambers, wherein the third reactant chamber includes a liquid impermeable, gas permeable membrane; and
a first frangible seal separating the first and third reactant chambers and a second frangible seal separating the second and third reactant chambers, the first and second frangible seals isolating the first and second reactants;
wherein upon opening of the first and second frangible seals the first and second reactants mix and react to produce a gas.

23. The reaction vessel of claim 22, wherein at least one of the first reactant and the second reactant includes a liquid.

24. The reaction vessel of claim 22, wherein at least one of the first reactant and the second reactant includes a solid.

25. The reaction vessel of claim 22, wherein the first reactant is selected from a group consisting of acetic acid and citric acid and the second reactant is selected from a group consisting of sodium carbonate and sodium bicarbonate.

26. The reaction vessel of claim 22, wherein at least one of the first and second reactant chambers includes a gas-permeable membrane.

27. The reaction vessel of claim 22, wherein the third reactant chamber is disposed between the first and second reactant chambers.

28. A reaction vessel, comprising:
a first reactant chamber containing a first reactant;
a second reactant chamber containing a second reactant in combination with the first reactant chamber; and
a frangible seal separating the first and second reactant chambers and isolating the first and second reactants;
wherein upon opening of the frangible seal the first and second reactants mix and react by foaming to produce a foam composition selected from the group consisting of a facial cleaner, soap, surface cleaner, disinfectant, anti-microbial agent, and combinations thereof.

29. The reaction vessel of claim 28, wherein at least one of the first reactant and the second reactant includes a liquid.

30. The reaction vessel of claim 28, further comprising a third reactant chamber in combination with the first and second reactant chambers, wherein the third reactant chamber is separated from at least one of the first and second reactant chamber by a frangible seal.

31. The reaction vessel of claim 30, wherein the third reactant chamber includes a porous material and the foamed composition can permeate the porous material.

* * * * *